Nov. 27, 1956 E. A. MAY Re. 24,241

INJECTION APPARATUS

Original Filed May 17, 1949

INVENTOR.
Edwin A. May
BY
Duell and Kane
ATTORNEYS

United States Patent Office

Re. 24,241
Reissued Nov. 27, 1956

24,241

INJECTION APPARATUS

Edwin A. May, Glen Rock, N. J., assignor to Becton Dickinson and Company, Rutherford, N. J., a corporation of New Jersey Original No. 2,642,062, dated June 16, 1953, Serial No. 93,771, May 17, 1949. Application for reissue June 11, 1954, Serial No. 436,268

10 Claims. (Cl. 128—173)

Matter enclosed in heavy brackets [ ] appears in the original patent but forms no part of this reissue specification; matter printed in italics indicates the additions made by reissue.

This invention relates to a structurally and functionally improved injection apparatus by means of which medicament may be hypodermically injected into tissue without the use of a penetrating needle. *This application discloses certain subject matter in common with my application Ser. No. 12,597, filed March 2, 1948, now abandoned in favor of my pending application Ser. No. 206,482, filed January 17, 1951, and also claims certain subject matter disclosed in said applications.*

It is an object of the invention to furnish a unit of this character which may be readily loaded and operated and by means of which, moreover, the depth or velocity of injection may be regulated with nicety.

Additionally, by means of the present invention, the volume of injected medicament may be controlled so that a precise dosage may be injected according to the judgement of the physician.

Still another object is that of furnishing an injection apparatus which may be used or handled with safety even though the operator possesses no technical skill; the present invention additionally contemplating an apparatus of the type which will include relatively few parts each individually simple and rugged in construction and which parts may be readily assembled to furnish a unitary apparatus operating with freedom from all difficulties over long periods of time.

With these and other objects in mind, reference is had to the attached sheet of drawings illustrating one practical embodiment of the invention and in which.

Figure 1:
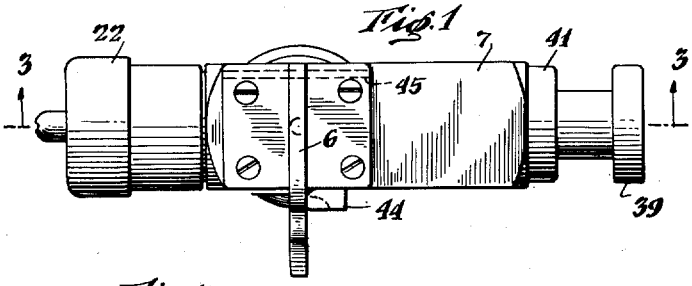
Fig. 1 is a top plan view.
Figure 2:
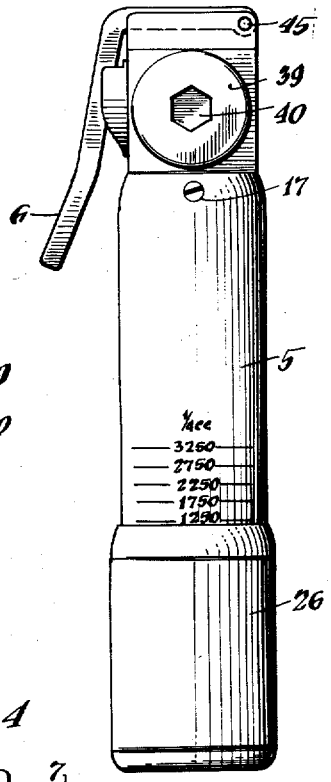
Fig. 2 is a rear view of the assembly.
Figure 3:
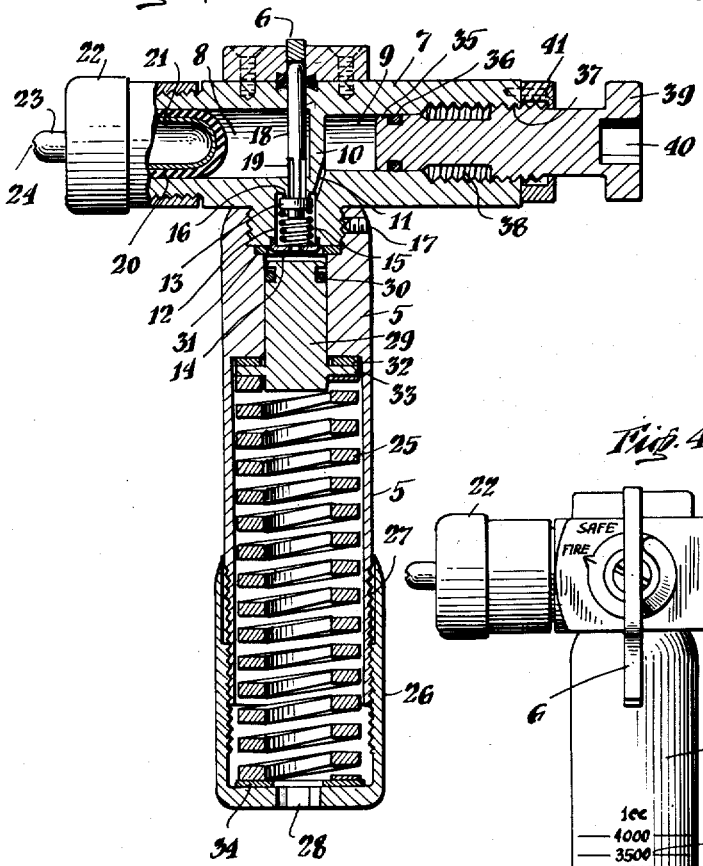
Fig. 3 is a sectional side view taken along the lines 3—3 and in the direction of the arrows as indicated in Fig. 1.

In these views the numeral 5 indicates a downwardly extending or handle portion and the numeral 6 indicates an operating lever or trigger. The latter is mounted by a head portion 7 which is conveniently formed with opposed bores 8 and 9 separated by a central partition 10. A passage 11 may extend between the chamber or bore 9 and a valve chamber 12. Mounted within the latter is a valve 13 and apertured retaining member 14. A spring 15 urges valve 13 against its seat 16. A separation of the handle 5 from the head 7 may be prevented in any desired manner such as by means of a set screw 17. A stem 18 mounts or bears against valve 13 and this stem is formed with channels 19 through which liquids may pass from chamber 12 to bore 8.

Within that bore or chamber 8 a medicament-injecting assembly is provided. This may take one of several different forms. Conveniently, however, it includes a collapsible container or sack 20 preferably formed of rubber and which may in turn contain an ampule or capsule 21 of suitable material within which the medicament is packaged. The several parts may be retained against displacement by a cap 22 beyond which a nozzle 23 extends. That nozzle may have its outer end pierced to provide a relatively fine aperture 24 through which a column or jet or medicament may escape.

Within the handle 5 an accumulator structure is disposed. According to the teachings of the present invention such structure will, in its preferred concept include a spring 25 of relatively heavy type. The opposite ends of the spring will bear against a cap and piston respectively. The cap has been shown at 26 and is formed with threads which cooperate with threads 27 formed on the exterior of the handle 5. This cap is also conveniently formed with an opening 28 which may have a configuration such that it will cooperate with a wrench and will also serve to vent air from within the interior of the handle 5. The piston has been indicated at 29. A packing 30 is associated with the piston and the body of the latter slides within the accumulator cylinder defined adjacent the upper end of handle 5. A suitable seal 31 may be disposed between handle 5 and the stud extending from head 7. A washer 32 may be interposed between the end of the main bore of handle 5 and a flange 33 forming a part of the piston. A washer 34 may also be interpose between the lower or outer end of spring 25 and the inner face of cap 26. Such elements will cushion the several parts of the assembly.

A further piston 35 is slidably mounted within the cylinder provided by the bore 9. A packing 36 may be carried by this piston. An enlarged portion of the body of the latter may be threaded as at 37 and cooperate with threads 38 formed in the rear end of bore 9. Beyond this portion the piston body is enlarged to furnish an operating head 39 conveniently formed with a socket 40 which may receive the end of a wrench. A retaining and closure element 41 may be applied to the rear end of head 7.

Figure 4:
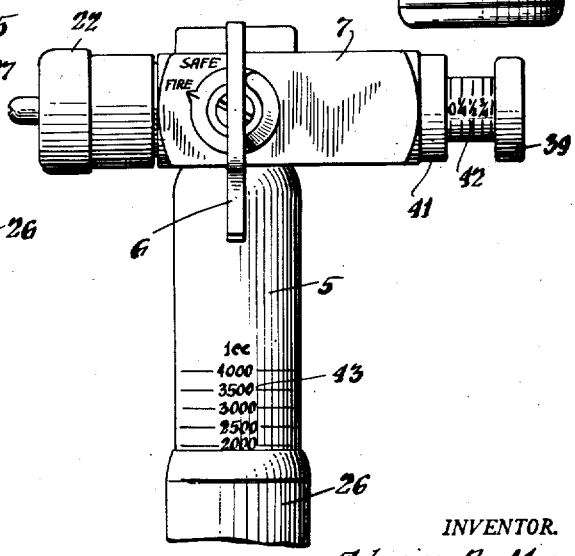
Fig. 4 is a fragmentary side elevation of the apparatus as shown in Figs. 1 and 2.

As shown especially in Fig. 4, the stem portion of piston 35 extending beyond the element 41 may be formed with graduations and indicia interpretative of those graduations as indicated at 42. These indicia may be read and registered with the outer edge or surface of the element 41. Columns of graduations and indicia such as have been indicated at 43 may be applied to the outer face of handle portion 5. These latter indicia may be read by registering with the same the leading edge of cap 26. In this connection it will be obvious both with respect to piston 35, as well as cap 26, that these units may be axially shifted or adjusted and that such adjustments will serve to bring into individual registry the calibrations as embraced in groups 42 and 43.

With a view to providing a structure which will prevent the trigger or handle 6 from being accidentally operated, a rotatable member in the form of a cam 44 may be mounted on the side face of head 7. The trigger or handle is pivotally supported as, for example, at 45 and overlies the stem 18 of the valve. It is apparent that when the cam is adjusted to the "Safe" position, it will underlie the edge of trigger 6 and prevent the same from operating or shifting stem 18. However, when cam 44 is rotated to the "Fire" position, then this handle or trigger may be swung around its pivot to shift or project stem 18 and the adjacent valve 13.

In use it will be understood that the bores, cylinder and passages may contain a body of air-free liquid. The medicament chamber receives either a capsule, an ampule, a cartridge or even a pre-determined amount of unpackaged fluid medicament. The cartridge or ampule—if employed—may be formed of metal, foil, plastic, gelatin or any other proper substance and embody any proper configuration and assembly consistent with the structure of that chamber. After the chamber is loaded or charged then the cap 22 or its functional equivalent is mounted upon the head 7. Assuming that the dosage to be injected is ¼ or ½ cc. then the head 39 will be rotated either by engaging its knurled surface or by means of a suitable wrench so that the selected graduation aligns with the surface of element 41.

As previously brought out, cap 26 is capable of adjustment with respect to the handle 5. According to the depth of the injections to be given, the viscosity of the medicament and other determinable factors, the operator will adjust that cap with respect to the handle by aligning the leading edge of the former with the desired graduation 43 on the face of the latter. Such adjustment will be consistent with the volume of the dosage as determined by the position of piston 35. In other words, the operator will read that column of graduations 43 which is identified by a designation corresponding to the value of the graduation 42 which corresponds to the volume to be injected. In adjustment it is apparent that piston 35 will be projected inwardly. It is also apparent that the inward movement of piston 35 will displace a portion of the liquid filling the cylinder or bore 9. The quantity so displaced will correspond to the dosage which is to be injected. The displaced liquid will flow through passage 11, the aperture or apertures in the retainer 14 and act against the head of piston 29 to shift the latter against the thrust of spring 25. The apparatus is now ready for use subject only to shifting the cam or other safety structure to a position at which the parts may be released.

In such use nozzle 23 will normally be brought into direct contact with the skin overlying the area of tissue to be injected. The aperture 24 may conveniently be in direct contact with such skin surface. If now the trigger or handle 6 is depressed it will rock around pivot 45 thereby depressing stem 18 and unseating valve 13. Under those circumstances, liquid will be free to flow from the accumulator cylinder within which piston 29 is enclosed through the aperture of retainer 14, past the valve and its seat 16, through the grooves 19 and so into chamber 8. Incident to the pressures under which the liquid is placed, such flow will result in a collapse of the sack 20 and an expulsion of the medicament in the form of a fine stream and at velocities such that it will penetrate the tissues. Thereafter the handle 6 may again be released and the safety shifted to assure against a subsequent accidental discharge. If a structure other than the sack 20 is employed, then the liquid will nevertheless act against the surfaces provided to assure the desired results. The ejection will be almost instantaneous, but will vary with the adjustment of the accumulator.

If a dosage has been used which resulted in only part of the medicament within chamber 20 being expelled, then the balance of such medicament, or any desired fraction thereof could be subsequently injected in the same or another patient. This would be accomplished by further adjusting piston 35 to displace the desired amount of liquid into the accumulator. Thereupon the latter, if necessary, could be adjusted and the injection step proceeded with.

With the medicament exhausted, cap 22 may be dismounted and the fragments of, or collapsed body of the medicament-containing unit may be removed and discarded. Piston 35 will be retracted. A new unit may be positioned within bore 8 or a suitable portion of the latter may be filled with liquid medicament. Thereupon the cap is reapplied. It is apparent that during this operation liquid may freely displace from bore 8 incident to the check valve action on the part of valve body 13. Such displaced liquid will flow through the upper portion of chamber 12 and through the vent passage 11 towards chamber 9. The entire aforedescribed cycle may now be repeated.

Thus, among others, the several objects of the invention as specifically aforenoted are achieved. Obviously numerous changes in construction and rearrangement of the parts might be resorted to without departing from the spirit of the invention as defined by the claims.

I claim:

1. An injection apparatus including in combination a casing portion to mount a unit containing a body of medicament to be discharged through an orifice at high velocity, said apparatus providing in communication with said casing portion spaces and passages to receive liquid to operatively act against the medicament to expel the same through the orifice, an accumulator comprising a spring, a piston connected to said spring and extending into one of said spaces and a valve for controlling the flow of liquid from such latter space to said casing portion.

2. An injection apparatus including in combination a casing portion to mount a unit containing a body of medicament to be discharged through an orifice at high velocity, said apparatus providing in communication with said casing portion spaces and passages to receive liquid to operatively act against the medicament to expel the same through the orifice, an accumulator comprising a spring and an enclosure therefor to always maintain said spring in partially compressed condition, a piston connected to said spring and extending into one of said spaces to be shifted by the liquid therein, a valve for controlling the flow of liquid from such latter space to said casing portion and means for adjusting the tension of said spring.

3. An injection apparatus including in combination a casing portion to mount a unit containing a body of medicament to be discharged through an orifice at high velocity, said apparatus providing in communication with said casing portion spaces and passages to receive liquid to operatively act against the medicament to expel the same through the orifice, an accumulator comprising a spring, a piston connected to said spring and extending into one of said spaces, a valve for controlling the flow of fluid from such latter space to said casing portion, means for adjusting the tension of said spring and means for indicating the degree of such adjustment.

4. An injection apparatus including in combination a casing portion to mount a unit containing a body of medicament to be discharged through an orifice at high velocity, said apparatus providing in communication with said casing portion spaces and passages to receive liquid to operatively act against the medicament to expel the same through the orifice, an accumulator comprising a spring, a piston connected to said spring and extending into one of said spaces, a valve for controlling the flow of liquid from such latter space to said casing portion and shiftable means for displacing liquid from one of said spaces and through one of said passages to cause a shifting of said piston and [compresison] *compression* of said spring.

5. An injection apparatus including in combination a casing portion to mount a unit containing a body of medicament to be discharged through an orifice at high velocity, said apparatus providing in communication with said casing portion spaces and pasages to receive liquid to operatively act against the medicament to expel the same through the orifice, an accumulator comprising a spring, a piston connected to said spring and extending into one of said spaces, a valve for controlling the flow of liquid from such latter space to said casing portion, shiftable means for displacing liquid from one of said spaces and through one of said passages to cause a shifting of said piston and compression of said spring and means for registering the amount to which said latter means have been shifted.

6. An injection apparatus including a head portion formed with opposed bores and passages connecting said bores, one of said bores receiving medicament to be expelled at high velocity, said bores and passages being adapted to contain operating fluid, shiftable fluid displacing means disposed in the other bore, an accumulator comprising a cylinder connected to said passages, a piston within said cylinder, compressible means acting against said piston to urge the same to resist displacement of fluid into said cylinder and a valve interposed in the passage between said cylinder and said medicament-receiving bore.

7. An injection apparatus including a head portion formed with opposed bores and passages connecting said bores, one of said bores receiving medicament to be expelled at high velocity, said bores and passages being adapted to contain operating fluid, shiftable fluid displacing means disposed in the other bore, an accumulator comprising a cylinder connected to said [pasasges] *passages,* a piston within said cylinder, compressible means acting against said piston to urge the same to resist displacement of fluid into said cylinder, a valve interposed in the passage between said cylinder and said medicament-receiving bore, manual means for shifting said valve and safety means for normally preventing such shifting.

8. An injection apparatus including a head portion formed with opposed bores and passages connecting said bores, one of said bores receiving medicament to be expelled at high velocity, said bores and passages being adapted to contain operating fluid, shiftable fluid displacing means disposed in the other bore, the other bore being formed with a thread throughout its outer portion and providing a cylinder adjacent its inner portion, a piston slidable within said cylinder, the body of said piston extending outwardly and being formed with threads to engage the thread bores, an operating portion extending beyond said threaded body and an accumulator connected to said passages and storing under pressure the fluid displaced by said piston.

9. An injection apparatus including a head portion formed with opposed bores and passages connecting said bores, one of said bores receiving medicament to be expelled at high velocity, said bores and passages being adapted to contain operating fluid, shiftable fluid displacing means disposed in the other bore, the other bore being formed with a thread throughout its outer portion and providing a cylinder adjacent its inner portion, a piston slidable within said cylinder, the body of said piston extending outwardly and being formed with threads to engage the thread bores, an operating portion extending beyond said threaded body, registering means for indicating the degree of projection of said piston within said cylinder portion and an accumulator connected to said passages and storing under pressure the fluid displaced by said piston.

10. An injection apparatus including in combination a casing portion to receive a body of medicament to be discharged through an orifice at high velocity, an accumulator forming a part of said apparatus and comprising a cylinder, a piston within said cylinder and compressible means acting against said piston to urge the same to resist displacement within said cylinder, said apparatus being formed with a further cylinder and passages connecting said cylinders and said casing portion and means for displacing fluid within said last named cylinder, through one of said passages and into said first named cylinder to shift the piston within the latter.

[11. A hypodermic injection apparatus including in combination a hollow body providing adjacent one of its ends a space to receive a medicament-containing ampule from which liquid is to be discharged at high velocity, a loading cap movably mounted by said body to close said space, a compressible pressure accumulator disposed within said body and operatively connected to said space to act on an ampule contained therein, manually operated force-compounding means carried by said body for compressing said accumulator, means for retaining said accumulator in compressed condition and manually shiftable means accessible on the exterior of said body to release said retaining means.]

[12. A hypodermic injection apparatus including in combination a hollow body providing adjacent one of its ends a space to receive a medicament-containing ampule from which liquid is to be discharged at high velocity, a loading cap movably mounted by said body to close said space, a compressible pressure accumulator disposed within said body and operatively connected to said space to act on an ampule contained therein, said apparatus being formed with a fluid passage extending to said accumulator, manually operated force-compounding means carried by said body to force fluid under pressure towards said accumulator for compressing the latter, means for retaining said accumulator in compressed condition and manually shiftable means accessible on the exterior of said body to release said retaining means.]

[13. A hypodermic injection apparatus including in combination a hollow body providing adjacent one of its ends a space to receive a medicament-containing ampule from which liquid is to be discharged at high velocity, a loading cap movably mounted by said body to close said space, a compressible pressure accumulator disposed within said body and operatively connected to said space to act on an ampule contained therein, said apparatus being formed with a fluid passage extending to said accumulator, said apparatus being also formed with a cylinder communicating with said passage, a piston movable in said cylinder to displace fluid therefrom through said passage and to act against said accumulator for compressing the latter, a manually rotatable plunger operatively connected to said piston and having screw threaded engagement with said body whereby upon said plunger being turned said piston will be projected, means for retaining said accumulator in compressed condition and manually shiftable means to release said retaining means.]

References Cited in the file of this patent or the original patent

UNITED STATES PATENTS

| | | |
|---|---|---|
| 2,322,244 | Lockhart | June 22, 1943 |
| 2,322,245 | Lockhart | June 22, 1943 |
| 2,380,534 | Lockhart | July 3, 1945 |
| 2,390,246 | Folkman | Dec. 4, 1945 |
| 2,398,544 | Lockhart | Apr. 16, 1946 |

FOREIGN PATENTS

| | | |
|---|---|---|
| 11,272 | Great Britain | Aug. 14, 1884 |